United States Patent [19]

McMillan et al.

[11] Patent Number: 5,283,598
[45] Date of Patent: Feb. 1, 1994

[54] ILLUMINATION OF THE CORNEA FOR PROFILOMETRY

[75] Inventors: Charles F. McMillan, Livermore; William D. Fountain, Fremont; Carl F. Knopp, San Mateo, all of Calif.

[73] Assignee: Phoenix Laser Systems, Inc., Fremont, Calif.

[21] Appl. No.: 842,879

[22] Filed: Feb. 27, 1992

Related U.S. Application Data

[63] Continuation-in-part of Ser. No. 656,722, Feb. 19, 1991, Pat. No. 5,170,193, which is a continuation-in-part of Ser. No. 456,109, Dec. 22, 1989, Pat. No. 5,054,907.

[51] Int. Cl.$^5$ .............................................. A61B 3/10
[52] U.S. Cl. ..................................... 351/212; 351/247
[58] Field of Search ................... 351/212, 247; 356/376

[56] References Cited

U.S. PATENT DOCUMENTS 4,312,574  1/1982  Wilms ................................. 351/212
4,878,750  11/1989  Sekiguchi ........................... 351/212

Primary Examiner—Rodney B. Bovernick
Assistant Examiner—Hung Xuan Dang
Attorney, Agent, or Firm—Thomas M. Freiburger

[57] ABSTRACT

An improved apparatus and technique are disclosed for illuminating the cornea with points of light for analysis of the specularly reflected return light in determining the shape of the cornea. In combination with an optical illumination system which forms real images of points of light inside or in the path of the objective lens, the system of the invention includes a plurality of real light source points optically peripheral to the real image points and physically outside to the objective lens. The sources of the point light sources may be optical fibers or LEDs arranged in an array which optically extends radially outward from the objective lens, although the external points may be forward or back from the objective lens. The two types of point light sources are generally registered in a pattern and together form an ordered geometric array for providing paraxial reflections off the cornea over a wide area of the cornea, including both central and peripheral areas of the cornea.

11 Claims, 4 Drawing Sheets

ILLUMINATION OF THE CORNEA FOR PROFILOMETRY

REFERENCE TO RELATED APPLICATION

This application is a continuation-in-part of application Ser. No. 656,722, filed Feb. 19, 1991, now U.S. Pat. No. 5,170,193, which was a continuation-in-part of application Ser. No. 456,109, filed Dec. 22, 1989, now U.S. Pat. No. 5,054,907, both of which are incorporated herein by reference.

BACKGROUND OF THE INVENTION

The invention is concerned with ocular diagnostics, and more particularly it relates to an improved system for profilometry of the cornea by detecting the apparent location of point sources of light as reflected paraxially from the cornea. The invention encompasses the profilometry system and also a subsystem which provides an array of point light sources to enable profiling of the cornea over a wide area.

U.S. Pat. No. 5,054,907 disclosed a system for detecting the shape of the central portion of the cornea, including that region immediately around the optical axis (e.g. the central 2 mm.). That patent is incorporated herein by reference. The technique and system disclosed in the patent involved forming virtual point light sources inside the objective lens of a diagnostic system, or between the objective lens and the patient. The virtual point light sources were real images of point light sources. This brought an array of point light sources directly adjacent to the optical axis (the array may extend across the optical axis), thus enabling the profilometry of a central region of the cornea which was difficult to profile with previous equipment involving light sources strictly peripheral to the objective lens.

The patented system included use of the objective lens as a field lens for the paraxially reflected pattern image, in order to expand the region of coverage on the cornea. However, profiling widely enough to include outer regions of the cornea along with the central region would still be a problem unless a very "fast" objective lens (i.e. having high numerical aperture) were used, which may need to be objectionably large or positioned objectionably close to the eye.

An example of a previous perimeter device with peripheral light sources is shown in Wilms Patent No. 4,312,574. None of the perimeter devices was capable of efficiently providing point light sources useful to image all important regions of the cornea, including near the optical axis.

Achatz et al. Patent No. 4,159,867 is also somewhat pertinent to this invention. However, the apparatus shown in that patent used a different set of reflected rays, and also used, in a preferred embodiment, a cardoid-shaped surface. In addition, the disclosed device did not project a set of target spots through the refractive optics, which comprised a visual telescope rather than a system for delivery/collection of treatment, ranging, tracking or viewing channels. The system preferably used as small a telescope as possible, located in the plane of the cardoids, and the patent indicated it was preferred not to use a video camera for detection of the reflected rays.

A combination of peripheral, external point light sources with the patented system just described was disclosed in copending application Ser. No. 656,722, now U.S. Pat. No. 5,170,193, referenced above. The present invention includes variations and improvements on the system disclosed in the copending application.

SUMMARY OF THE INVENTION

The invention described herein combines the advantages of the profiling light source arrangement disclosed in U.S. Pat. No. 5,054,907 with an additional arrangement which is mounted radially externally to the objective lens of the diagnostic system, i.e. peripheral with respect to the objective lens. Together the two types of light sources form an ordered array of point light sources including virtual light sources and real light sources, for reflection from the corneal surface. To the eye and to the diagnostic apparatus, all points of light in the profiling arrangement appear to lie in an ordered geometric pattern in and about the objective lens, which may be about 50 millimeters away from the eye. In this way, the system of the invention integrates the real, perimeter point light sources located radially outside the lens with the real-image light sources located inside the lens. The result is a diagnostic array which presents much more of the area of the cornea for profilometry, and associated analytical and computer equipment can calculate the shape of the corneal surface.

In a preferred embodiment of the invention an illumination system for use in an ophthalmic diagnostic instrument or profilometry instrument provides an ordered array of light points for reflection paraxially off a wide area of the cornea including a central region of the cornea. The illumination system includes means for forming a pattern of discrete separated point light sources and forming a real image of the pattern of point light sources at a position located between the interior of the objective lens and the patient's eye. The real image includes point light sources in positions which are very close to or directly on the optical axis. Further included in the illumination system are a plurality of external light source points, optically peripheral to and outside the real image points and physically external to the objective lens. A support means stably supports the external light source points in fixed relationship to the objective lens. The two types of light points, i.e. the real image of point light sources and the external light source points, are generally registered optically in a composite array and together form an ordered geometric array for providing paraxial reflections off the cornea over a wide area of the cornea, including near the center of the cornea.

The plurality of external light source points of the illumination system may comprise ends of optical fibers external to the objective lens. In another embodiment, the external light source points can comprise an array of light emitting diodes positioned optically peripheral to the real image points.

In a further alternative embodiment, the external light source points are provided through a molded light-transmissive body, through which light is projected from an external, radial illumination means. The light transmissive body has an internal mirror surface which reflects the light forward to a plurality of terminal points at the front of the body, to form the external light source points.

It is therefore among the objects of the invention to provide a method, procedure and instrument which are capable of profiling a majority of the surface of the cornea, without requiring a large objective lens or one located extremely close to the eye. A related object is to accomplish this in an efficient and compact arrangement which integrates two types of point light sources at or near the end of the objective lens. These and other objects, advantages and features of the invention will be apparent from the following description of preferred embodiments, considered along with the accompanying drawings.

DESCRIPTION OF PREFERRED EMBODIMENTS

Figure 1:
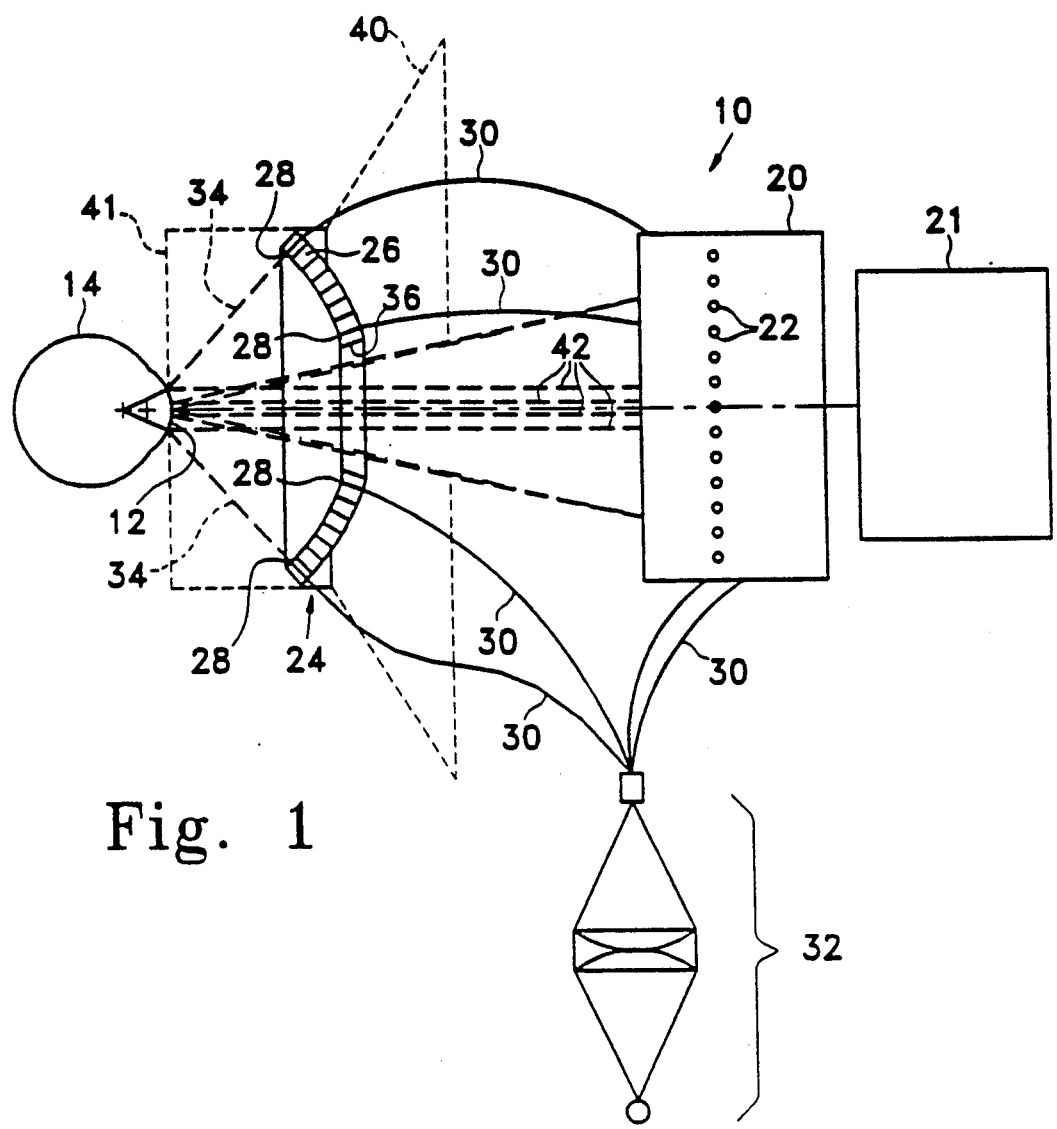
FIG. 1 is a schematic view showing a cornea profiling system in accordance with the principles of the invention.

In the drawings, FIG. 1 shows schematically a system 10 for illuminating the cornea 12 of a patient's eye 14 for profilometry of the cornea. The system 10 includes an objective lens end element or front lens element 20, which is equivalent to the objective lens element 20 shown in the drawings of U.S. Pat. No. 5,054,907, incorporated by reference herein. That patent should be referred to for disclosure of additional optics (which would be to the right of the lens element 20 of FIG. 1 herein) for forming a real image of point light sources either inside the objective lens (it may be inside the element 20 as shown) or in front of the element 20, between that element and the patient's eye 14. The phrase "between the objective lens and the patient" or a similar expression as used herein is intended to mean inside the objective lens or in front of the objective lens.

The referenced patent also discloses apparatus, methodology and a mathematical approximation that can be used to derive the shape of the cornea from a projected pattern of light sources. The other optics, which may be similar to those described in Pat. No. 5,045,907, are indicated at the box 21 in FIG. 1.

The system and apparatus of the present invention combine the advantages of the profiling light source arrangement described in the referenced patent with an additional, external point source arrangement generally identified as 24 which extends the target source radially outside the optical system itself. As shown in FIG. 1, a target extender frame or expander plate 26 supports an array of point light sources 28 which, in this example, are the termini of a plurality of optical fibers 30. The optical fibers 30, shown emanating from a light source 32, form a target source extension array which is outside the objective lens element 20 and which is optically radially peripheral to the real-image point light sources 22 formed in accordance with Pat. No. 5,054,907, which may be inside the objective 20 as shown.

Figure 1A:
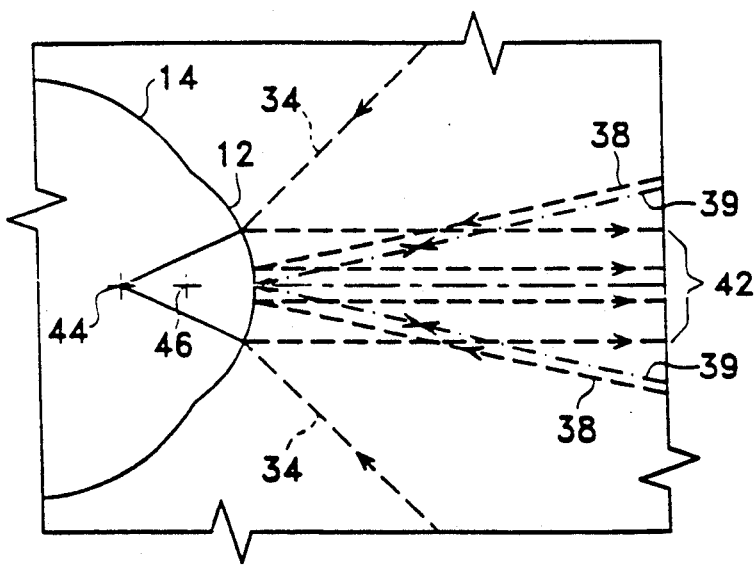
FIG. 1A is a detail taken from FIG. 1, showing light rays at the cornea.

FIG. 1 and FIG. 1A show selected outer light rays 34 from outer fibers of the target extender frame 26, which is of outer dimensions and spacing from the eye such that the patient's nose and cheek bones are ideally avoided by these outer rays 34 from the periphery of the frame (some of the outermost rays 34 may be blocked by the nose in some cases). The plate 26 has a central hole 36 for passage of those profilometry rays 38 which come from the real image light source points 22 inside the objective (or in front of the objective), and for passage of a ranging beam represented by selected rays 39 in FIGS. 1 and 1A and possibly for passage of other beams not shown. A depth tracking subsystem which may be used is described in copending application Ser. No. 655,919, filed Feb. 19, 1991, now 5,162,641, assigned to the same assignee as the present invention and incorporated herein by reference.

A dashed-line trapezoidal box 40 in FIG. 1 indicates an approximate locus for avoidance of the nose and cheek bones, on either side of the eye. The locus is shown symmetrical because the eye can be either eye of the patient. Another dashed-line box 41 indicates a region within which the equipment may be too close to the patient and may contact the nose, cheek bones, brow, etc.

FIG. 1 and particularly FIG. 1A also show reflected canonical profilometry rays 42, returning toward the objective lens 20 and the analytical equipment for use in profiling of the cornea.

As generally indicated in FIG. 1, the extender frame or plate 26 may comprise a segment of a spherical shell centered on the location of the virtual focus of the cornea (half way from the center of curvature 44 of the cornea to the surface of the cornea, this location being indicated at 46). The plate may have an outer frame 52, shown in FIG. 2, to support the plate, or the outer frame may be integral with the expander plate. The extender plate 26 is shown somewhat schematically in frontal elevation in FIG. 2.

Figure 2:
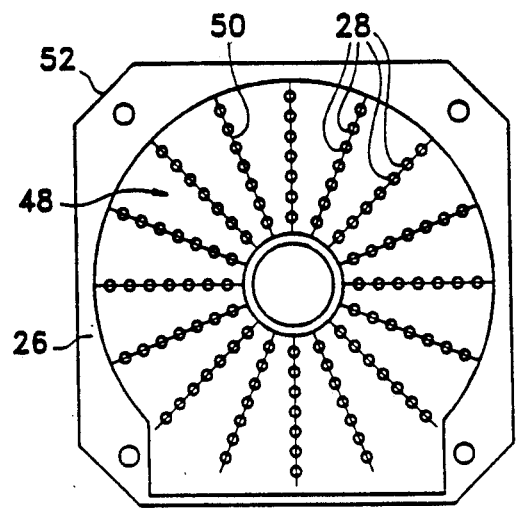
FIG. 2 is another schematic view, showing a pattern of point light sources of the system of the invention, in frontal view essentially as seen by the patient.

The target pattern 48 can comprise, as an example, a multiplicity of holes through the shell or plate 26 in a radial pattern, as shown by lines 50 in FIG. 2. Each of these holes is illuminated axially, in this preferred embodiment by the terminus of an optical fiber secured in the hole. These form the array of external point light sources 28 discussed above.

The illumination bundle from each point light source 28 includes those rays that will be reflected from the eye in a direction parallel to the axis of the objective (paraxially). The rays technically are reflected from a tear layer on the cornea, although the reflection is sometimes referred to herein and in the claims as being from the cornea or from the eye.

As stated earlier, the two types of light points, i.e. the real image of point light sources from the objective and the peripheral, external light source points 28, are generally registered optically in a composite pattern and generally form an ordered geometric array for providing the needed paraxial reflections off the cornea for profilometry of a wide range of the cornea. However, the registration of these two parts of the composite light source pattern is mechanically not critical, and the term "generally registered" is intended to include some lack of registry in the mechanical sense, although the two types of point sources are in similar patterns capable of registration. The registry of the points can be done electronically, during a calibration routine carried out by a microprocessor of the system. However, good reproducibility of the position of the extender plate 26, which may be mechanically mounted on a swing arm (not shown) for moving away from the position shown in FIG. 1 when necessary, will obviate the necessity to recalibrate the system each time the extender is moved out of, then into, the working position.

Instead of the plate 26 shown in FIGS. 1 and 2, the array of external point light sources 28 can be supported with arms or radial segments (not shown), each of which contains a pattern unit, the target as a whole being made up of a series of such arms or segments. Further, the external light source arrangement can be more easily fabricated if the array surface is a plane rather than a segment of a sphere, and will still function well enough to yield desired accuracy of data. (In the case of a planar array of fiber ends, it is preferable that those ends not be both plane and polished, nor cleaved.)

As another modification of the external light source arrangement shown in FIG. 1, the external light source points can comprise a multiplicity of LEDs positioned on a mounting frame such as the shell-shaped plate 26 of FIG. 1 or a planar plate, arranged in the desired pattern. Although LEDs are not specifically illustrated, FIG. 2 can be considered to show LEDs, as an alternative, at the points 28.

Figure 3:
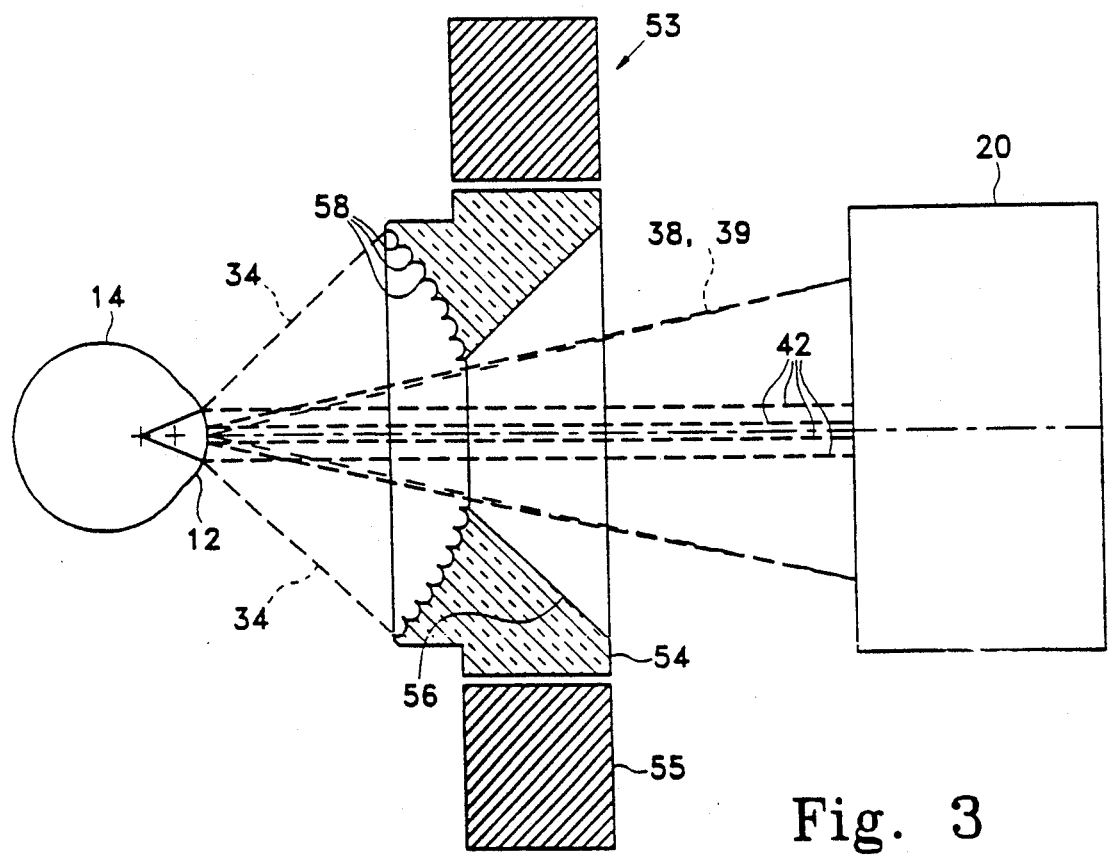
FIG. 3 is a schematic view of similar to FIG. 1, showing another embodiment of the invention.

FIG. 3 shows a system similar to that of FIG. 1, with an objective lens element 20 positioned as shown in FIG. 1, but with a modified form of external light source generally identified as 53. In this embodiment a molded target source extension 54, which may be of a transparent plastic material or moldable glass having good light transmission characteristics, receives light projected radially inwardly from a ring illuminator 55. The light traveling radially inwardly is reflected off the internal reflective conical surface 56 of the molded component, to a multiplicity of small projections 58 in an array as desired. These tips 58 may be polished for good light transmission, the surfaces between the projecting tips 58 being shaped so as not to transmit light toward the cornea but rather to reflect it back internally or, where this is not practical, to transmit it away from the cornea. Other configurations will be apparent to those skilled in the art.

Selected light rays 34, 38, 39 and 42 shown in FIG. 3 are similar to those illustrated in FIGS. 1 and 1A.

Figure 4:
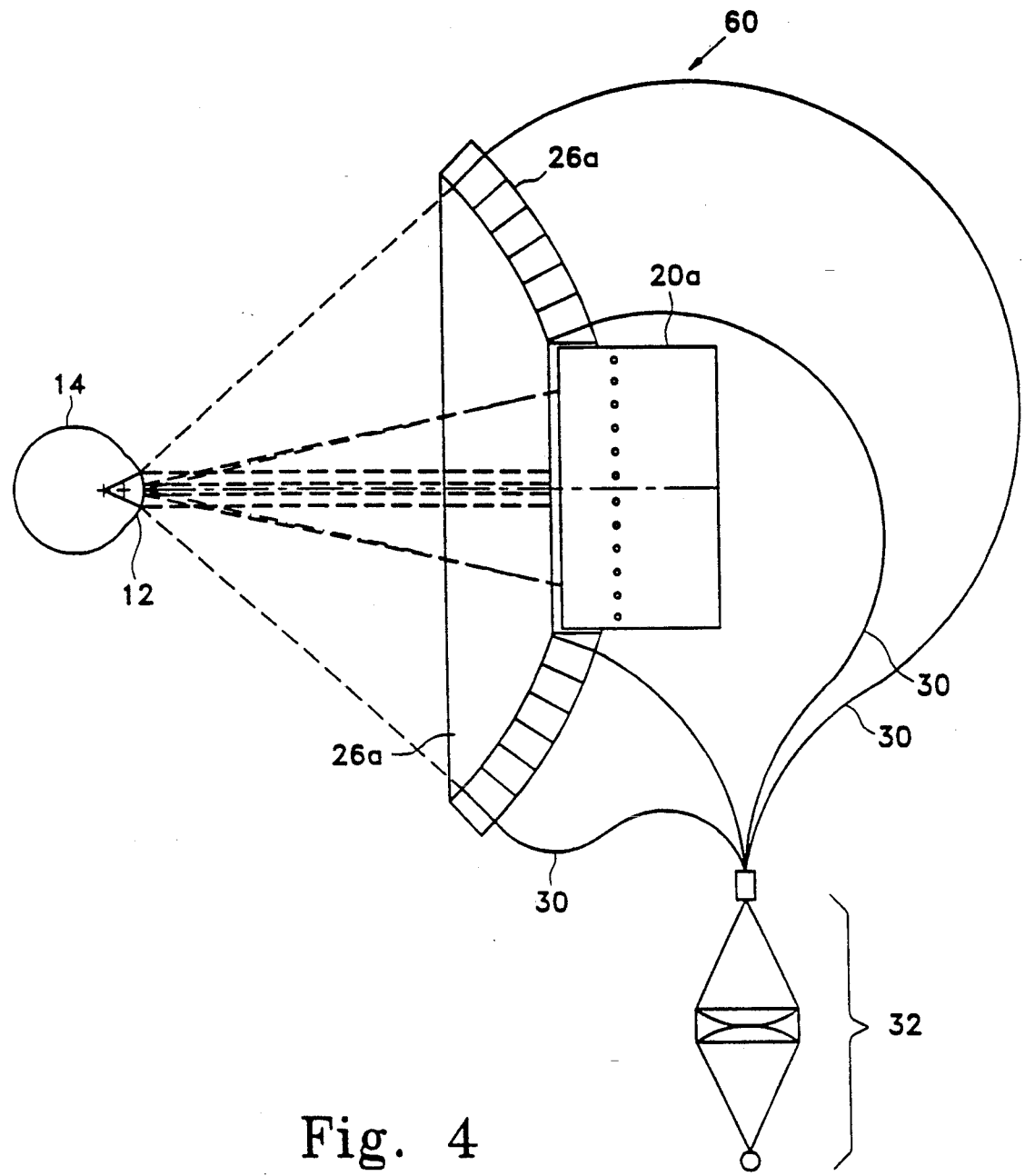
FIG. 4 is a schematic view similar to FIG. 1, but showing another modified embodiment.

FIG. 4 shows another modified embodiment of the invention. The system 60 of FIG. 4 is similar to that of FIG. 1, except that the target source extender 26a is positioned approximately at the same distance from the eye as an objective lens element 20a, instead of the objective and the target extender being axially offset as in FIGS. 1 and 3. The extender plate or target source extension 26a may thus be mounted directly on or so as to clear the objective 20a, and it will not be necessary to move the target extension. The embodiment of FIG. 4 is advantageous over those shown in FIGS. 1 and 3 in the case of the use of the equipment associated with the system for procedures on the eye which are outward from the cornea and widely off-axis. By moving the target extender 26a back from the eye, and making it correspondingly larger, the target extender is not physically in front of the objective 20a and thus cannot limit the range of rays which can approach the eye from the objective.

Figure 5:
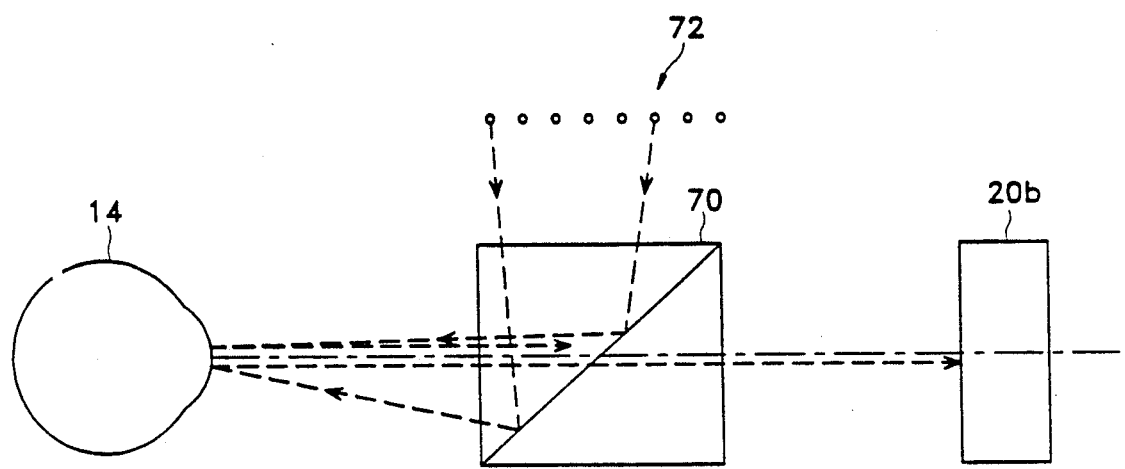
FIG. 5 is a schematic view showing another embodiment of the invention.

Another modified embodiment is shown in the schematic view of FIG. 5. In this embodiment, a beam splitter (such as a 50—50 beam splitter) is positioned between the eye 14 and the objective lens element 20b. A full light point array 72 is positioned off-axis as shown, and is mirrored axially toward the eye by the beam splitter. The array 72 provides all light points of the pattern, including the central portion of the pattern which was generated by real image points in the objective, in the earlier described embodiments. The advantage of the arrangement shown in FIG. 5 is simplicity, since only one source is involved, obviating any problems with mechanical registration of inner and outer portions as in other embodiments. Disadvantages which may arise from this arrangement are the need for a relatively large beam splitter, the placing of another object in front of the patient's eye, and the light intensity loss caused by the beam splitter.

Another possible arrangement, not illustrated in the drawings, is to use a small beam splitter to mirror onto the axis only the central portion of the light point array. The remaining, outer points of the pattern can then be supplied by a target extender having a central opening as in FIG. 1, placed just in front of the small beam splitter. In this case, registration of the two types of point sources is necessary mechanically or electronically, but generally only once, and most of the light source points do not suffer beam splitter losses.

The profilometry system and illumination system described herein may be used in an automated laser surgery system such as described in application Serial No. entitled "Automated Laser Workstation for High Precision Surgical and Industrial Interventions", filed on the same date as this application, assigned to the same party as this application and incorporated herein by reference.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. An ophthalmic diagnostic instrument for determining the shape of the cornea of a patient's eye, comprising:

an objective lens as an optical element of the instrument, on an optical axis of the instrument and generally at the front of the instrument, means for forming a pattern of discrete separated point light sources and forming a real image of the pattern of point light sources at a position located between the interior of the objective lens and the patient's eye, the real image including point light sources in positions which are very close to or directly on the optical axis, a plurality of external light source points, optically peripheral to and outside the real image points and physically external to the objective lens, support means for stably supporting the external light source points, fixed relative to the objective lens, the two types of light points, that is the real image of point light sources and the external light source points, being generally registered optically in a composite pattern and together forming an ordered geometric array for providing paraxial reflections off the cornea over a wide area of the cornea, including near the center of the cornea, means for collecting preferentially rays reflected paraxially off the cornea from the composite pattern, and means for analyzing the pattern, which may be distorted, generated by these returned, collected rays and for comparing it to an undistorted reference pattern, including means for analyzing the relative location of rays from the two patterns, and including means for deriving mathematically a close approximation of a corneal surface shape that would give rise to such a collected pattern.

2. The instrument of claim 1, wherein said means for comparing to an undistorted reference pattern includes means for generating said undistorted reference pattern by reflection of the composite pattern of light points from a calibration ball.

3. The instrument of claim 1, wherein the plurality of external light source points comprise ends of optical fibers external to the objective lens and positioned optically peripheral to the real image points.

4. The instrument of claim 1, wherein the plurality of external light source points comprise an array of LEDs positioned optically peripheral to the real image points.

5. The instrument of claim 1, wherein the plurality of external light source points comprise a molded light-transmissive body having a generally circular exterior and a central opening on the optical axis of the instrument, external illumination means for projecting light radially into the body from the circular exterior, internal means for reflecting such light generally forward toward the patient, and light point means formed integrally at a front side of the body for receiving the internally reflected light and projecting the light as said plurality of external light source points.

6. A method for determining the shape of the cornea of a patient's eye using an ophthalmic diagnostic instrument having an objective lens as an optical element of the instrument, on an optical axis of the instrument and generally at the front of the instrument, comprising:

forming a pattern of discrete separated point light sources and forming a real image of the pattern of point light sources at a position located between the interior of the objective lens and the patient's eye, the real image including point light sources in positions which are very close to or directly on the optical axis, placing a plurality of external light source points at positions optically peripheral to and outside the real image points and physically external to the objective lens, stably supporting the external light source points, in fixed position relative to the objective lens, the two types of light points, that is the real image of point light sources and the peripheral light source points, being generally registered optically in a composite pattern and together forming a generally geometric array for providing paraxial reflections off the cornea over a wide area of the cornea, including near the center of the cornea, collecting preferentially rays reflected paraxially off the cornea from the composite pattern, and analyzing the possibly distorted pattern generated by these returned, collected rays and comparing it to an undistorted reference pattern, including analyzing the relative location of rays from the two patterns, and deriving mathematically a close approximation of a corneal surface shape that would give rise to such a collected pattern.

7. The method of claim 6, wherein the comparing step comprises comparing the possibly distorted pattern to an undistorted reference pattern generated by reflection of the composite pattern of light points from a calibration ball.

8. In an ophthalmic diagnostic instrument for determining the shape of the cornea of a patient's eye, such instrument having an objective lens as an optical element of the instrument on an optical axis of the instrument and generally at the front of the instrument, an illumination system for providing an ordered array of light points for reflection paraxially off a wide area of the cornea including a central region of the cornea, comprising:

means for forming a pattern of discrete separated point light sources and forming a real image of the pattern of point light sources at a position located between the interior of the objective lens and the patient's eye, the real image including point light sources in positions which are very close to or directly on the optical axis, a plurality of external light source points, optically peripheral to and outside the real image points and physically external to the objective lens, support means for stably supporting the external light source points, fixed relative to the objective lens, and the two types of light points, that is the real image of point light sources and the external light source points, being generally registered optically in a composite pattern and together forming an ordered geometric array for providing paraxial reflections off the cornea over a wide area of the cornea, including near the center of the cornea.

9. The illumination system of claim 8, wherein the plurality of external light source points comprise ends of optical fibers external to the objective lens and positioned optically peripheral to the real image points.

10. The illumination system of claim 8, wherein the plurality of external light source points comprise an array of LEDs positioned optically peripheral to the real image points.

11. The illumination system of claim 8, wherein the plurality of external light source points comprise a molded light-transmissive body having a generally circular exterior and a central opening on the optical axis of the instrument, external illumination means for projecting light radially into the body from the circular exterior, internal means for reflecting such light generally forward toward the patient, and light point means formed integrally at a front side of the body for receiving the internally reflected light and projecting the light as said plurality of external light source points.

* * * * *